United States Patent [19]

Greene et al.

[11] Patent Number: 5,573,954
[45] Date of Patent: Nov. 12, 1996

[54] METHOD OF OBTAINING SMALL REPRESENTATIVE SOLID-PHASE SAMPLES

[75] Inventors: Malbone W. Greene, Vista; Don Isenberg, Carlsbad; Charles Walbourn, Encinitas, all of Calif.

[73] Assignee: Microbics Corporation, San Diego, Calif.

[21] Appl. No.: 467,207

[22] Filed: Jun. 6, 1995

Related U.S. Application Data

[63] Continuation-in-part of Ser. No. 853,109, Mar. 18, 1992, Pat. No. 5,426,035.

[51] Int. Cl.$^6$ ..................................................... G01N 1/00
[52] U.S. Cl. .......................... 436/174; 436/28; 436/172; 436/177; 73/863; 435/29; 435/39
[58] Field of Search ........................... 436/28, 172, 174, 436/175, 177, 176, 178, 179; 73/863; 366/140, 273, 274; 435/29, 39, 822, 968

[56] References Cited

U.S. PATENT DOCUMENTS

| | | | |
|---|---|---|---|
| 4,144,134 | 3/1979 | Plakas | 195/103.5 M |
| 4,283,490 | 8/1981 | Plakas | 435/8 |
| 4,513,280 | 4/1985 | Hannan et al. | 340/632 |
| 4,689,305 | 8/1987 | Stiffey et al. | 435/291 |
| 4,950,594 | 8/1990 | Stiffey | 435/35 |

OTHER PUBLICATIONS

Bulich et al., "Measurement of Soil and Sediment Toxicity to Bioluminescent Bacteria When in Direct Contact for a Fixed Time Period", *Water Environment Federation*, 65th Annual Conf. & Exposition, New Orleans, LA, Sep. 20–24, 1992, pp. 52–63.

*Primary Examiner*—Jill Warden
*Assistant Examiner*—Harold Y. Pyon
*Attorney, Agent, or Firm*—Fitch, Even, Tabin & Flannery

[57] ABSTRACT

A method of obtaining small representative solid-phase samples from a large solid-phase sample. Solid-phase material is optionally separated from any liquid-phase that may be present and is mixed. A portion of the mixed solid-phase particulate sample is selected which provides an intermediate size representative sample. After adding liquid diluent to the intermediate particulate sample in a vessel, the suspension is agitated to promote separation of small particles as may be adhering to large particles to obtain a homogeneous suspension. Agitating is preferably carried out using a magnetic stirring bar. Fractions of this homogeneous suspension are then obtained by aspirating using a pipette and transferred to test tubes which will constitute small, truly representative solid-phase particulate samples from which replicate testing can be confidently performed.

14 Claims, No Drawings

METHOD OF OBTAINING SMALL REPRESENTATIVE SOLID-PHASE SAMPLES

This application is a continuation-in-part of our U.S. application Ser. No. 07/853,109 filed Mar. 18, 1992, now U.S. Pat. No. 5,426,035.

FIELD OF THE INVENTION

This invention relates to methods for obtaining small representative samples from a large solid-phase sample and more particularly to obtaining a plurality of representative replicate samples which facilitate, for example, quantitative measurement of the toxicity of a solid-phase substance.

BACKGROUND OF THE INVENTION

Soil and sediment toxicity test methods currently in use (cf. Geisy, John P. and Robert A Hoke, *Freshwater Sediment Toxicity Bioassessment: Rationale For Species Selection And Test Design*, in J. Great Lakes Res. 15(4): 539–569) include:

a. the use of benthic organisms (which spend a significant portion of their lives in contact with sediments or soils) such as midges (mayfly larvae), clam larvae and earthworms, using parameters ranging from weight gain to percentage of test organisms surviving a timed exposure (days) to the solid particulate samples as the measure of toxic effect;

b. measurement of the toxic effects on algae;

c. determination of the effect on germination of seeds, and the growth rate of roots of sprouting seeds;

d. determination of the effect on fertilization of sea urchin eggs;

e. determination of lethality to higher organisms (e.g. mysid shrimp, dahpnia, fish) during a timed exposure (days), to either water or organic solvent (diluted with water) elutriates from the solid particulate samples;

f. changes in the light output of bioluminescent microorganisms when exposed to sample elutriates for relatively short times, such as 5 to 30 minutes (the Microtox® System, marketed by Microbics Corporation, Carlsbad, Calif.);

g. bioluminescent bacteria in direct contact with the solid particulate sample for about 20 minutes (the method of K. K. Tung, et al., described in U.S. patent application Ser. No. 07/682,923), which enhances response to sparsely soluble toxicants, a kit for the performance of which is currently being marketed by Microbics Corporation as the "Solid-Phase Test".

These methods, except the tests using benthic organisms, are all based on the well established art of testing water for acute toxicity. The most recent adaptation of a water acute toxicity test for the testing of solid particulate samples is the bioluminescent microorganism test utilizing direct contact between the solid particulate sample and the test microorganism, with filter separation of microorganisms from particulates before light readings are taken (Tung et al.). It is the most rapid and least expensive method available. In addition, this method typically results in toxic response data for a plurality of concentrations of the solid-phase sample, permitting the investigator to generate a dose-response curve, which is potentially a great advantage. A dose-response curve is a graph of the varying responses of a test organism to varying concentrations of the substance being tested. A reasonably smooth, monotonic curve is indicative of a definite functional relationship between the two variables. Traditionally, toxicologists have relied on the existence of such a dose-response curve not only for determining the toxicity quantitatively, but also as prima facie evidence that there is truly a causal relationship between the observed effect and the concentration of the substance tested. The quantitative result is usually reported as the LC50 (lethal concentration for 50% destruction) for aquatic organisms, and LD50 (lethal dose for 50% destruction) for mammalian toxicity results. For luminescent microorganisms, it has become conventional to report EC50, the effective concentration causing 50% light loss. More recently, however, the U.S. Environmental Protection Agency (EPA), Environment Canada and others have recommended making a distinction by using EC50 for "quantal" data (i.e. end-points resulting in a defined "effect", such as death, of 50% of the test organisms), and IC50 for the concentration causing a 50% "inhibition" of a measured functional parameter, a good example of which would be the reduction of light output from the luminescent bacterium, *P. phosphoreum*, in a Microtox® toxicity test. This Specification uses the IC50 convention, in anticipation of its general acceptance in the near future.

Data for several concentrations are not readily obtainable with tests employing benthic organisms. Due to the difficulty of performing tests with such organisms, they are most often exposed only to 100% of the test and reference samples, making the test semi-quantitative. Because of the speed and low cost of the luminescent microorganism test method of Tung et al., it is common practice to generate a dose-response curve for every test, providing additional assurance that there is a causative relationship. There are, however, several potential sources of error when bioluminescent microorganisms are mingled directly with solid particulate samples. This is true of both the method of K. K. Tung, et al., and the similar method described by H. Brouwer, et al., *A Sediment-Contact Bioassay With Photobacterium Phosphoreum*, in Environmental Toxicology and Chemistry, vol. 9, pp. 1353–1358, 1990.

One major source of concern is the difficulty of separating the particulates from the microorganisms before determining the toxic effect of the sample on the light output of the microorganisms, and another is the assurance that the relatively small sample being tested is truly representative of the total sample. Three major factors with regard to operational and theoretical difficulties are:

Factor 1; the possible optical interference of particulates, which cannot be totally separated from the microorganisms by filtration and/or by centrifugation;

Factor 2; the possible loss of microorganisms from the suspension due to adherence to the particulates at the time the separation is performed, whether by filtration, centrifugation or simple settling;

Factor 3; the demonstrable fact that the microorganisms solubilize, in effect, sparsely water-soluble toxicants in/on the solid particulate sample makes it very difficult to distinguish between a true toxic response and interferences from factors 1 and 2, above.

The uncertainties in data interpretation are compounded by the fact that "clean soils", soils which appear to be nontoxic when aqueous elutriates are tested, normally appear to be moderately toxic (e.g. 50% light loss for only one or two percent sample) when tested by the method of Tung et al. It is probable that some, if not all, of the light reduction is due to factors 1 and 2, above, but it is also quite possible that water-insoluble toxicants in and on the clean soil particles are bioavailable to the microorganism when in direct contact, and the clean soil is actually toxic to the bacteria. All three factors may be expected to depend on the physical properties of the particles, which means that soils from different locales may not have the same interference-to-real toxic response ratios. As a result, there has been some reluctance among users of this test to report the ICxx determined. (By convention, the ICxx is that concentration of sample which causes an xx % loss of light after a specified exposure time. IC50, a 50% light loss, is most often reported by users of the Microtox System.) A rigorous method for relating the results to those which the same sample would yield if it were free of interferences from factors 1 and 2, above, is lacking. This lack causes some users to treat the test results, which are otherwise inherently capable of providing quantitative answers, as if they are merely qualitative.

Using test and data handling approaches which are different from those of Tung et al., Brouwer et al. (p 1356, op.cit.) used only five toxicity ranks (severe, high, intermediate, low and very low) to characterize the toxicity of sediments they tested from Hamilton Harbor, Ontario, Canada. They tested only one fixed concentration and reported the toxic response of each sediment tested as the "% Photobacterium activity relative to control". The control sample was, in this case, an aliquot from a large (30 liter) sample collected from site 46, located four (4) or more km from the major sources of industrial pollution. The control sample (reference sample) and up to six other sediment samples were tested at the same fixed concentration, as a "batch", and the toxic response of each sample tested was assigned one of the qualitative toxicity ranks with respect to the toxicity of the control. The control sample was tested with every batch.

It is probable that all natural soils and sediments contain detectable quantities of sparsely soluble toxicants, such as metal salts and organics. It is reasonable, therefore, to be concerned with additional toxicity (e.g. added by man's activities) when surveying a site for toxicity. For example, the toxicity of soils/sediments relative to that of the pristine soil/sediment of the locale is the major interest when pollution assessment is the objective. The desired measurement in this case is the toxicity of each sample tested relative to that of the clean soil/sediment of the same locale. Until the present invention, there has been no method for determining the entire dose-response curve of a test sample relative to that of a reference sample, and the questions of how and where to obtain the correct clean soil/sediment reference sample at the beginning of a large survey project have not been answered in an economically feasible way. There has also been great difficulty in obtaining replicate samples for which there is confidence that they will be truly representative of the sample as a whole.

It is also desirable that the raw information for every sample tested be available, without any modification, to make the results relative to any other test. For example, a sample having a small unmodified IC50 (highly toxic) might be selected as the reference sample in the belief that it was improbable that it could have been contaminated by man. If a large number of samples of similar toxicity were to be compared to it by the method of Brouwer et al. the operator might conclude, erroneously, that they were all nontoxic. Upon discovery of the error, recovery could require retesting all samples using a new reference sample. Such a mistake could not occur if an IC50 were to be determined from raw data for every sample, assumed reference included, using the method of Tung et al. However, the IC50 values so determined would all be independent of each other, and prior to this invention there was no method for determining the relative toxicities from such independent test results.

As it has been practiced prior to this invention, the method of Tung et al. has used a very small (on the order of 0.4 grams) solid-phase sample. While the requirement for a very small sample has some advantages, it has been discovered that the sample size is a major factor contributing to the variance of IC50 in repeat tests of "the same sample". In effect, it has not been feasible to take a truly representative sample aliquot which is that small. The precision of the Tung et al. test is adequate for ranking of test samples, but it is marginal for purposes of determining the toxicity of samples relative to that of a reference sample of comparable toxic/interference responses, in accordance with the method of the present invention.

Similarly, when toxicity ranking alone is desired, it is not necessary to control the reaction temperature in practicing the invention of Tung et al. However, in practicing the method of the present invention, it is necessary to control the incubation temperature at the same value for all tests performed, in order to permit subsequent reduction of any and all data sets against any other as the reference sample. The preferred temperature is 15° C., but any standardized temperature in the range of about 10° to 30° C. may be selected for use on a given toxicity survey program.

A similar need for relative toxicity determination exists in the field of acute and chronic water toxicity measurement by bioassay. There are many cases in which it is desirable to determine the toxicity of water before and after another source of toxicant is added, or before and after treatment intended to reduce the toxicity. Using the method of this invention, for example, the toxicity of the water in a stream could be determined relative to what it is/was on any given day for which data are/become available.

In summary, the current state of the art lacks a practical, economic means of rigorously determining the toxicity of a water or solid particulate sample relative to that of another sample. In particular, there has not been a method of generating a dose-response curve for one such sample relative to the other prior to this invention, nor has there been a method for confidently assuring that replicate samples were truly representative.

SUMMARY OF THE INVENTION

One object of this invention is to provide a rigorous method of reducing toxicity test results obtained for a first sample against those obtained in a different test of a second sample, herein after referred to as the "test sample" and the "reference sample", respectively.

It is a further object of this invention to provide a method of reducing test sample data for a plurality of concentrations against that obtained for a plurality of concentrations of the reference sample, making it possible to determine an ICxx for the test sample from a dose-response curve having each point relative to the corresponding point for the reference sample.

It is also an object of this invention to provide a method which does not require measurement of the reference sample every time one or more test samples are tested for toxicity.

It is a further object of this invention to provide a method whereby an entire set of test sample data files from many sites, such as might be generated over many weeks of testing during an assessment of the toxic loading of sediments in a large area of a river bottom, may be reduced against any other test sample data file as the reference sample.

Yet another object is to provide a method for obtaining truly representative small samples from a large sample to permit replicate samples to be run with confidence.

These and other objects and advantages are achieved by the method of the invention, which comprises:

a. obtaining toxic response data for a plurality of concentrations of at least two different test samples, including reagent controls having zero sample concentration for each sample;

b. defining the sample having the smallest toxic response at high concentrations as the reference sample;

c. computing the toxic response of the test sample relative to that for the reference sample for at least two concentrations in accordance with the equation:

relative gamma=$\Gamma_R$=$(L_{SC}/L_{SX})(L_{RX}/L_{RC})$−1, where $L_{SC}$=light output of the test sample control (i.e. for X=0), $L_{SX}$=light output of the test sample for concentration X, $L_{RX}$=light output of the reference sample for concentration X, $L_{RC}$=light output of the reference sample control (i.e. for X=0); and d. generating a dose-response curve of concentration versus relative $\Gamma$ (gamma) for at least two corresponding concentrations of the two samples.

$\Gamma$ (gamma) is defined as the ratio of light lost to light remaining, and has been shown to be the preferred measure of toxic response, both theoretically and experimentally (see Johnson, Frank H., Henry Eyring and Betsy Jones Stover, *The Theory Of Rate Processes In Biology And Medicine*, John Wiley & Sons, N.Y., N.Y., 1974).

The appropriate equation for step c, above, if using "relative light loss", the time-honored measure of toxic response, is:

relative light loss=1−$(L_{SC}/L_{SC})(L_{RC}/L_{RX})$, where all factors are defined as above.

It should be noted that the method is also applicable to lethality tests using organisms other than bioluminescent microorganisms. For use with lethality tests of shrimp, daphnia, fish, etc... simply replace the words "light output of" with "fraction of organisms surviving in" in the definitions of the four different "L" values of step c. Microorganisms are preferred because they may be grown, harvested and freeze-dried under carefully controlled conditions. When reconstituted for testing they have, therefore, a well-defined prior history, which assures that the response to toxicants can be reproduced between laboratories and from lot-to-lot of freeze-dried microorganisms. It is not economically feasible to achieve the same level of uniformity of test results with higher organisms. Consequently, it may be that the requirement for reproducibility of results over periods of years may warrant use of a reference sample for microorganism-based tests which use carefully standardized microorganisms or for in vitro enzyme inhibition tests which use purified enzymes.

Other objects, advantages and features of the present invention will become apparent from the detailed description which follows.

DETAILED DESCRIPTION OF THE PREFERRED EMBODIMENTS

The overall invention provides methods of determining the toxic responses for various concentrations of a test sample of water or of suspended solid particulate matter such as soils, sediments and spent-sludges relative to the toxic responses for the same concentrations of any desired less toxic reference sample. The three major factors causing concern with regard to interpretation of test results for solid-phase samples, enumerated above, are avoided by use of particular features of the procedures, as explained in detail below.

The optical interference of residual particulates (factor 1, above) in the bioluminescent bacterial test is a complicated function of the physical properties of the sample. Important physical properties include the distributions of particle size, shape, reflectivity, absorbtivity, and refractive index, as well as the concentration of particulates. Similarly, the loss of microorganisms due to adherence to the solid particles when they settle-out and during final filter separation (factor 2, above) will depend on the same physical properties and, possibly, on the nontoxic chemical composition as well. Loss of light due to loss of bacteria resulting from adherence to particles because of any toxic property of the particles may be considered to be a part of the true toxic response for purposes of this Specification. All of the physical properties noted above, and the nontoxic chemical composition of soils and sediments, can vary widely from one geographical area to another. However, in general, they are semi-constant for a given locale within an area of interest. Consequently, it is normally possible to select a reference sample which is representative of the physical and nontoxic chemical make-up of all the samples obtained from a given locale. To the extent that the goal of selecting a reference sample which has the same make-up and, therefore, interfering characteristics due to factors 1 and 2 is achieved, the toxicity test results for test samples will be corrected for the interferences by use of the method of this procedure. Moreover, with respect to each large sample collected for testing, it is important to obtain a truly representative small sample for testing or several such small samples for replicate testing, and one feature of the procedure of the overall invention facilitates the obtaining of such small, truly representative samples.

SELECTION OF THE REFERENCE SAMPLE

A "test locale" may be conveniently defined, for purposes of this Specification, as a locale in which the physical make-up of the soil/sediment is sufficiently uniform to assure that there will be acceptable variations in the physical and nontoxic chemical make-up of samples taken from any site within any locale so defined. "Acceptable variations" in the sample make-up are defined as the maximum variations which can be allowed without seriously compromising the objectives of the toxicity survey program. Obviously, the program team must make the judgement with regard to acceptable variations for every project, based on the project objectives. A major advantage of this procedure is that this important decision can be made after all samples have been tested, when all unmodified data are available to assist in making it. With this definition of a test locale, it is necessary to use a different reference sample for each test locale into which a survey area is divided. Again, with this procedure, the survey area may be divided into the minimum number of test locales consistent with the project objectives after samples from all sites are tested, and after having the opportunity of characterizing the make-up of every sample by visual examination. The parameters to be ranked during the visual examination are the particle color and size distributions in the settled solids of the highest concentration tested. Soils and sediments which do not have the same general appearance are not from the same locale, as defined herein. The results of such visual examinations, including a qualitative ranking of the turbidity of the tested aliquot for some fixed sample concentration (e.g. 10%), provide an adequate basis for establishing the boundaries of test locales except in cases with the most demanding survey objectives. In such cases, the settled solids and residual liquid from the highest concentration of every sample may be retained, and/or photographed in color, for future simultaneous visual comparisons in order to arrive at an optimum assignment of a large number of samples to the minimum number of test locales.

The advantage of establishing such test locales is that the interferences from factors 1 and 2, above, will be approximately constant for all samples obtained from each test locale, and a single reference sample may be employed to obtain consistent relative toxicity response data for all samples from each entire test locale. As noted above, an advantage of this procedure is that all samples may be tested and raw data files created without being concerned about selection of a reference sample. The direct IC50 values, i.e. those based upon raw data using no reference, provide very useful semi-quantitative toxicity data. The major potential relative errors due to lack of a reference sample effect the least toxic samples, for which the interferences due to factors 1 and 2 are greater than or comparable to the actual toxicity, including factor 3. For example, the Tung et al. method referred to above, which provides this type of raw data files, has small relative errors when the samples are more than moderately toxic (IC50 less than about 0.1%). The deficiency of that method for samples of low toxicity is met by the present procedure. After the fact, so to speak, the least toxic sample, which will have the largest IC50, may be designated as the reference sample for an entire test locale. All data files for samples from that locale may be reduced against it, to provide relative IC50 values, if and when desired.

The present procedure can always provide useful data for the relative toxicity of all sites within a test locale. Its applicability is unquestionable when there is at least one sample of low toxicity (e.g. IC50 of about 1% (w/v) or more, comparable to that for most "clean soils") within the locale. If all samples tested from a test locale are toxic (e.g. IC50 of 0.5% or less) it is possible, but may not be advisable, to use the least toxic of them as a reference sample for all the others. The objectives of the survey must be considered when the project team makes such choices, since the reference sample concept may not be particularly applicable in such cases. In this event, the survey project team may elect to create a clean reference sample having the desired composition of particle types by making a mixture of uncontaminated soils of the desired types. An approach for preparing a representative synthetic clean soil sample is given in the Final Report for Contract Number 68-03-3413, Richard P. Traver, contract officer, performed for the U.S. Environmental Protection Agency by PEI Associates, Inc. Being an expensive alternative, this is the preferred approach only when it is required to assure that the major goals of an area survey will be met. A major advantage of this procedure is that the decision with regard to choice of reference sample can be made after the bulk of the work of a survey is completed, when the choice can be based on the facts rather than on speculation.

A rather crude sample make-up classification system based on visual physical characteristics such as those which are used to define test locale boundaries (e.g. relative amounts of sand, humus, clay, particle size-range, turbidity and color of a 10% (w/v) solution after settling for a fixed time, etc. . .) is often adequate for establishing several suitable reference samples for survey projects. In this case, data for each sample are reduced against the reference sample (that having the least toxicity) having the same sample make-up classification. This method of selecting appropriate reference samples is not dependent upon sample site locale per se, but upon the visual similarity of sample make-up. The choice of reference samples remains the responsibility of the project team.

TEST METHODOLOGY REQUIREMENTS

An advantage of the present procedure is that no choice of reference sample precludes subsequent data reduction using a different reference if, as and when desired. Although additional tests might occasionally be deemed desirable, no retesting is required to take full advantage of new experience and knowledge gained from later work on the same or any other project. The only restrictions are that the same test protocol be used in all tests, that the test organisms used for all tests be standardized (i.e. have the same response to toxic substances), that the small samples actually tested be truly representative, and that either the same concentrations be tested or the responses for corresponding concentrations be calculated from a fitted curve.

The restriction that the test organisms have uniform toxic response requires that they have the same genealogy and uniform life histories; i.e. be of the same strain, be of equal age and initial health, be equally nourished before and during the test, etc. . . The bioluminescent bacteria-based test (Microbics Corporation's Microtox System) meets this requirement by imposing standardized growth, harvesting, freeze-drying, storage, reconstitution and use conditions for the bacterial "reagent". It is not economically feasible to achieve this level of uniformity for any higher life form. The method of the present invention is applicable to the toxicity test results obtained with other organisms, but the quality of the final results can only be as good as the standardization of the test organism permits.

SELECTION OF SOLID-PHASE REFERENCE AND TEST SAMPLE ALIQUOTS

A major problem with solid-phase sample testing of all types results from the difficulty of obtaining a truly representative sample. One advantage of the bioluminescent bacterial solid-phase test (Tung et al.) is that very small samples are required (less than 0.5 g), but this can also be a disadvantage from the standpoint of taking a representative sample. From the laws of statistics, the mean of a larger sample better approximates the true mean of a population. The reproducibility of toxicity test results is generally poor when aliquots of less than one gram of a sample, which is a mixture of materials ranging in size from coarse sand (up to 2 millimeter diameter) through colloidal clay (less than one micrometer), are tested repeatedly. The importance of testing sample aliquots of like particle size distribution may be explained as follows.

The interaction between bacteria and sample particles when in direct contact is clearly a surface phenomena, as is the rate of solution of sparsely soluble toxicants. Both losses of bacteria in the separation step and solubilization of the toxicants which are not water-soluble (by the bacteria) are related to the total surface area of the particles. Dissolved toxicants, as well as those still bound in and on the solid-phase sample, contribute to the total toxic response of the test of Tung et al. The rate of solution and the ultimate solubility of toxicants in solid-phase samples also largely determine the response observed with any other aquatic toxicity or lethality test adapted to the measurement of solid-phase toxicity. The effect of total surface area of the sample is, therefore, an important factor in the observed toxicity of particles of the same chemical composition. Everything else being equal, the surface area, and, therefore, the measured toxicity of a given mass or volume of particles, would be expected to increase inversely with the mean particle size. For example, spherical stones of radii $r_1$ and $r_2$ (and, also, cubic stones of edges $r_1$ and $r_2$) have a surface ratio $S_1/S_2=(r_1/r_2)^2$, and a count ratio (for equal total mass, assuming constant density) which is given by $(r_2/r_1)^3$. This means that the 1,000,000 spherical stones having 1/100 the radius and the same volume as a single stone, will have 100 times the surface area of the single stone. A stone (spherical) having typical specific gravity of 2.7 with a diameter of 2 mm (0.079 inch) has a volume and mass of about 4.2 mm$^3$ and 0.011 g, which would be about 4% of a 0.3 g sample. If it is replaced by 1000 spherical stones of 0.2 mm (0.0079 inch) diameter the total surface area will increase ten-fold, and the measured toxicity contributed by this 4% of the total mass will increase. A better grasp of the situation may be obtained by viewing the reversed change: if all particles were 0.2 mm diameter spheres, replacement of the 1000 small particles by the one larger stone having 2 mm diameter could divide the contribution of that 4% of the total sample by a factor of up to 10, reducing its contribution to 0.4%, causing a net reduction in measured toxicity of 3.6%. If all particles were initially 0.02 mm instead of 0.2 mm, the total surface area would be 10 times greater, and the same mass of sample could potentially be 10 times more toxic even though it had the same composition and history of exposure to toxic pollutants.

It may be fairly concluded that, in real soil and sediment samples, much of the observed toxicity arises from the finest particles, representing a disproportionately small fraction of the total volume and mass. It is important, therefore, that the small sample aliquot being tested be typical with regard to particle size distribution to avoid highly skewed toxicity test results.

In addition to the importance of particle size distribution, the composition of the particulate matter may have an appreciable impact. As a consequence of the erosion and subsequent redeposition of old sedimentary and igneous rock formations, the nontoxic chemical composition of the particles within any given soil or sediment sample may also vary widely. An extreme example would be a mixture of quartz sand, humus and clay. Quartz sand, per se, should not be toxic, but it may have sparsely soluble organic and inorganic toxicants adsorbed on the surfaces. The generic term "humus" is used the describe soil derived from decayed or partially decayed organic matter. Humus would not normally be highly toxic (although some naturally occurring organic compounds are notoriously toxic), but humus absorbs sparsely soluble organics, such as petroleum products, pesticides; etc. Clay particles, in general, are very fine and adsorb organics. Clays also have a tendency to strongly adsorb toxic materials such as $Cu^{++}$ ion, effectively removing a portion of the ions from solution.

When using the test method of Tung et al. the toxic response to such adsorbed toxicants is frequently significantly greater than the response to water and organic solvent elutriates alone. A possible explanation of this fact is that the lipids in the cell wall of the bacteria "solubilize" the sparsely soluble toxicants. This seems like a plausible explanation for hydrophobic organics which are lipid-soluble, but it is less clear how inorganic toxicants (metal oxides and salts) are made more soluble. In any event, this important sensitivity advantage of the method of Tung et al. is somewhat negated by the marginal precision of the results, which is in part due to large variations in the actual composition of small sample aliquots taken in repeated tests. While the precision of the Tung et al. method is good compared with results of other biological tests of soils and sediments, it is very desirable to improve the precision of the overall procedure, particularly for testing samples of low to moderate toxicity. A specific improvement over the sample selection method of Tung et al. has been made. The improved sampling method, referred to herein as the "large sample procedure" (or LSP) to distinguish it from the Tung sampling method, which is referred to as the "small sample procedure" (or SSP), also makes it very easy to provide truly representative small replicates of a particular large sample when maximum precision is desired. The LSP is described in detail below.

LARGE SAMPLE PROCEDURE (LSP) FOR "n" REPLICATE TESTS

To reduce the impact of using very small samples on the precision of the Tung et al. method, a larger initial sample, though still quite small by most standards, is used. To further improve confidence in the results, replicate tests using truly representative aliquots from the larger sample suspension are performed. The preferred method of obtaining a truly representative small sample, using materials and apparatus which are readily available, is illustrated by the following example, in which twelve 1:2 dilutions of the sample and three controls are prepared for each of n (preferably two to ten) replicate tests of the sample. The sample dilutions prepared in accordance with this large sample procedure are subsequently subjected to tests in accordance with the Microbics Corporation's current published Solid-Phase Test Protocol (see Microtox® Manual, Volume 2, Detailed Protocols, 1992 Edition, pp 153–178).

STEP-BY-STEP LSP USED FOR SPECIFIC EXAMPLES PRESENTED a. thoroughly mix the solid-phase sample, then optionally centrifuge it (if a wet sediment) using any ordinary laboratory centrifuge if desired to separate water from the solids. After any such separation, decant the liquid phase and thoroughly mix the solids-fraction again to restore homogeneity throughout the entire sample. Then weigh-out 7.00 grams to provide an intermediate sample, eliminating atypical large particles (e.g. larger than about 5 mm (0.2 inch) maximum dimension, to avoid single particles having more than about 0.35 grams mass, which is about 5% of the total 7 grams, because such particles contribute relatively little to total surface area and therefore to the toxicity);

b. combine the intermediate solid sample with 35 ml of diluent in a clean 50 ml glass bottle, beaker or other vessel (e.g. borosilicate glass);

c. add a clean (preferably new) Teflon® covered magnetic stirring bar of appropriate size to the bottle so that it rests substantially flat on the bottom;

d. place the bottle on a magnetic stirrer, and adjust the stir rate to obtain a vortex depth of about 50% of the liquid level at the wall (while vortexing);

e. observe the contents of the bottle, interrupting stirring if required, and continue stirring until the solids are well separated into a suspension of coarse-to-very fine particles wherein the fine clay which normally adheres to larger particles have been washed therefrom as a result of the agitation from stirring with such a vortex);

f. while continuing to stir, use a pipette or pipettor with a tip aperture of at least 1.5 mm diameter and preferably not greater than about 2.5 mm to aspirate 1.5 ml of the solid suspension from a region generally adjacent to the wall (within about 4.5 mm from the wall) and about 2 cm (which is about 3 times the diameter of the spinning stir bar which rests on the bottom) above the bottom of the 50 ml bottle, and transfer such an aliquot of the sample suspension into tube 15 of each of "n" sets of 15 test tubes, where n is the number of replicate tests planned;

g. add 1.5 ml of diluent to the 15 tubes of each set, including tube 15 of each set, already containing a 1.5 ml aliquot of sample suspension;

h. make successive 1:2 serial dilutions in 11 tubes (for each of the n replicate tests) by transferring 1.5 ml of the resuspended solids from tube 15 to tube 14, then 14 to 13, 13 to 12, . . . and 5 to 4, mixing thoroughly before each transfer, and discarding 1.5 ml of the suspension from tube 4 of each set of 15 tubes.

Tubes 1, 2 and 3 of each of the n sets of 15 tubes are used as negative controls (nontoxic), and contain no sample.

In step a, the objective is to choose any appropriate size intermediate sample, usually between about 3 to 15 grams, and to avoid atypical particles when selecting the test aliquot. The suggested cut-off size of 5 mm is a rule of thumb. If particles of this size and larger are common they should be included in about the proportion found by examining several 7 gram samples, to avoid biasing the results toward high toxicity. It should also be noted that the use of 7.00 grams of sample in 35 ml of diluent is by way of example, it being obvious to one skilled in the art that the precision of the weight and that of the volume are the major requirements. The use of 7.37 grams in 31.67 ml, for example, would yield equally valid results, provided the actual numbers were to be used in calculating the concentrations. It reduces operator time to make an approximate 7 gram weighing, then use to the precise weight to calculate the actual concentrations tested, thus avoiding the tedium and inefficiency of weighing-out an exact 7.00 grams.

In steps b and c, a vessel between 20 and 100 ml is generally used, and liquid diluent, usually water, in an amount between about 15 and 75 ml is added. The vessel can be glass, or a polyethylene beaker will suffice. A standard stir bar for a 50 ml beaker is a rod about 3/16-inch in diameter. The speed of stirring is regulated to create a vortex cone height equal to about 30 to 70%, and preferably about 50% of the depth of the suspension along the wall of the vessel. Generally agitating for about 10 minutes will suffice.

In performing step f, the pipettor tip should be positioned above the spinning stirring bar on the bottom of the bottle high enough to assure that it does not become plugged by particles larger than the tip aperture, which will tend to remain at the bottom in the stirring zone that is created by the spinning stir bar, and exclusion of which particles will have a relatively minor impact on the measured toxicity once the fine particles have been washed from them, which occurs in step e. The preferred distance is about 2 cm for a 50 ml glass vessel.

SPECIFIC EXAMPLES ILLUSTRATING THE LSP AND RELATIVE TOXICITY METHOD

To verify the utility of the methods of this procedure for determining the toxicity of a sample relative to that of a reference sample, special software was generated for solving the above relative toxicity equation using an IBM compatible computer with any Microtox data file as the reference data for any other data file (having higher response at the highest concentration) accessible to the computer. The reference used was "clean soil", and the samples were SARM I AND SARM II, all obtained from the US EPA, and fully described in Final Report Number 68-03-3413, cited above. Briefly, the clean soil elutriates are nontoxic, and SARM I and SARM II are clean soil containing high organic/low metal and low organic/low metal additives, respectively.

Three groups of tests with clean soil were performed in accordance with the current Microbics Corporation Solid-Phase Test Protocol (the method of Tung et al.), with specific procedural modifications for evaluating the methods of this procedure as noted in the following discussion. For each group the mean responses obtained for each of twelve 1:2 dilutions were used to generate mean data files. The mean data files for each group of tests were then used as the reference sample data file for the data obtained for SARM I and SARM II. The clean soil mean file names assigned, and brief descriptions of the method of selecting the sample for each test of the three groups, were as follows:

1. File NORMALCS: The mean responses for fourteen tests using 0.3 gram clean soil samples suspended in 3 ml of Microtox diluent as the maximum concentration (SSP). The operator avoided larger (over 1 mm maximum dimension) particles in an attempt to improve reproducibility of results with 0.3 gram solid-phase sample aliquots.

2. File SPTREF01: The mean responses for ten tests of clean soil taken from several 7.00 gram samples suspended in 35 ml of Microtox diluent (LSP). The sample taken for each test was withdrawn with an Oxford 1 to 5 ml Macro Set® pipettor with type 814 tip (1.6 mm diameter tip aperture).

3. File CSREFNF2: The mean responses for ten tests of clean soil using the LSP performed exactly as were those for file SPTREF01, except that filtration was omitted from the Tung procedure, to investigate the possible variation in relative toxicity response due to losses of bacteria during filtration.

Replicate tests of SARM I with the SSP, and of SARM II with both the SSP and the LSP, were also performed. In the case of SARM II, tests were also performed using the LSP both with and without filtration. The unfiltered tests for both clean soil and SARM II were performed by removing 500 µL of the supernatant liquid from each of the reaction tubes containing the controls and serial dilutions of the sample with a micropipettor at the end of a twenty-minute incubation at 15° C., being careful not to stir the settled solids. The results of these tests are summarized in the following tables, in which:

Table 1 presents the IC50 and the 95% confidence range low and high values for IC50 for each of the four SARM I tests, and the means, standard deviations and coefficients of variation for the tests. For convenience in making comparisons, Table 1 also presents the relative toxicity results for SARM I using data files NORMALCS, SPTREF01 AND CSREFNF2 as the reference sample data in accordance with this procedure.

Table 2 presents data for five SARM II tests corresponding to that of Table 1 for SARM I, except that the results using file NORMALCS as reference sample for the four SARM II tests were not useful. (See the discussion in connection with Table 4, below.)

Table 3 presents data for four SARM II tests corresponding to that of Table 2, except that filtration was not employed for the SARM II tests presented in Table 3. Again, the results using the mean clean soil responses of file NORMALCS as the reference sample for the four unfiltered SARM II tests were not useful. (See the discussion of Table 4, below.)

Table 4 presents the mean $\Gamma$ responses used for files NORMALCS, SPTREF01 and CSREFNF2, and those for a typical SARM II test (file 09239102, filters used), plus the results of computing the responses relative to reference files NORMALCS and SPTREF01.

The IC50 and the "low" and "high" 95% confidence limits of IC50 are also given for each set of response data. In addition, the slope of the log-log dose-response curve for each set is given at the bottom of Table 4.

Table 1 shows quite clearly that the method of Tung et al. yields excellent results on a definitely toxic sample (raw IC50=0.038% (W/V), with no real need to correct against a reference sample. Specifically, the C.V. for every parameter presented in Table 1 is under 11%, which is better precision for solid-phase toxicity than can be achieved by other test methods, even at much higher cost, and the mean IC50 values determined against all three of the reference files lie well within the mean 95% confidence range determined for the raw SARM I data. With better than 95% confidence, therefore, there is no statistically relevant difference between the four mean IC50's. It should also be noted that the slopes of the log-log plots only have about a 7% spread, further indicating that the reference method of this invention may not be necessary for samples having an IC50 which is less than about one twenty-fifth that of the reference sample (i.e. twenty-five or more times as toxic). (See the IC50's given in Table 1 for SARM I and in Table 4 for the first two reference files.) This result is a logical consequence of high toxicity; the low concentrations of solid particles makc the interferences due to the three major factors discussed above essentially negligible at the sample concentrations of greatest interest, near IC50.

The SARM II results are of greatest interest with regard to the present procedure for compensation, because the most severe test of the relative toxicity method is for samples which differ only slightly from the reference sample. In this case, the mean raw data IC50 for SARM II shown in Table 2 differs from that of the three reference files by only about 5% for NORMALCS, a factor of 2.2 for SPTREF01 and a factor of 2.5 for CSREFNF2, given in Table 4. Table 2 illustrates that the Tung method as currently practiced, with SSP, also has very good precision at moderate toxicity levels (C.V. of 13.9% at raw IC50 of 0.654% (W/V) for SARM II). However, the precision of the relative responses against files SPTREF01 and CSREFNF2 is not as good, being 35.1% and 39.3%, respectively, for SPTREF01 and CSREFNF2. These C.V.s are almost three times that for the mean of the five raw SARM II files. This appears to be the result of the reduction of the mean responses due to computing the relative responses, which would not reduce the standard deviations of the raw responses. This result, therefore, illustrates the importance of improving the precision of the Tung et al. method by the practice of this method of compensation.

Table 3 presents the results of four replicate SARM II tests using one large sample in accordance with the LSP of this invention. Comparison to the corresponding results of SSP tests shown in Table 2 shows that the raw IC50 C.V. was reduced to 5.5% from 13.9%, a factor of 2.5 improvement. Equally important, there are similar improvements in the C.V.s of the low and high 95% confidence limits. Comparison of the IC50's for the relative responses of SARM II by SSP (Table 2) and by LSP (Table 3) against SPTREF01 and CSREFNF2 shows the distinct superiority of the LSP, for which the C.V.s are only about one-fourth and one-sixth as large. The C.V.'s for the low and high 95% confidence limits of IC50 are also greatly improved by use of the LSP.

The raw data log-log dose-response curve slopes shown in Tables 2 (for SSP) and 3 (for LSP) are not significantly different, which is consistent with the theory (Johnson et al.) that this slope is directly related to the response mechanism, rather than to the quantity of sample. Different slopes would be expected only if the SSP and LSP caused a difference in the toxicants actually taken in sampling, which is highly improbable.

It may be inferred from an examination of the data of Tables 2, 3 and 4 that selection of a proper reference sample, and taking truly representative test aliquots of both the reference sample and the sample, are all essential for the successful practice of this invention. The inability of the method to clearly detect the toxicity of SARM II with NORMALCS as the reference must arise from the fact that an excess of fine particles were used in this set of clean soil tests, giving this reference file about the same IC50 as SARM II. Since the response due to interferences only (all three clean soil reference files) does not have the same log-log slope as the combined interference and toxicant response of SARM II, it is not surprising that the relative Γ values for file 09239102 with NORMALCS as reference vary between positive and negative. The varying sign of Γ precludes use of many points for the log-log dose response curve (the log of a negative Γ is not defined) resulting in failure of the relative data to meet software criteria used to determine the reliability of the data. Consequently, the computer indicated that the data were inadequate for the determination of a log-log dose-response curve by linear regression. It should be noted, however, that this compensation method did not result in an error in toxicity ranking. However, if this method of compensation is not used, the operator can only report that SARM II is not toxic relative to file NORMALCS, which also is the first conclusion to be drawn from the data of Tables 2, 3 and 4. It is important to note, however, that the performance of the new method, even with the wrong reference, was actually quite good. Specifically, in Table 4, the highest Γ has been reduced from 347 to 3.07, over 100-fold, and the absolute value of the peak negative Γ is only about one-twelfth as large as the corresponding raw Γ. This might be expected, since the IC50's are almost equal, making the qualitative "relatively nontoxic" ranking inescapable. However, there is more information available to the operator when he reviews the Γ vs concentration results given in Table 4. The non-monotonic nature of the relative Γ response indicates that, although the sample and reference responses were about equal at IC50, they were not equal across the concentration range. From this fact it is clear that different reaction and/or interference mechanisms are involved, and the operator can infer that the reference sample is not the correct one for SARM II. The possibility that SARM II is significantly toxic (which, in fact, it is known to be) is left open, and further investigation is suggested.

The log-log slopes of Table 4 are essentially the same for all three clean soil files. This indicates that the mechanisms causing the responses are the same. While deliberate rejection of the large particles in taking the fourteen SSP samples made file NORMALCS appear to be about twice as toxic as the other two mean reference files, it has the same response mechanism. This, in turn, indicates that the response to the clean soil is either predominantly due to interfering factors 1 and 2, or the true toxic part of the clean soil response happens to have the same log-log dose-response curve slope that the non-toxic part has. To resolve the question, plate counts were performed on suitable dilutions of the residual material from a 10% (W/V) clean soil test tube after the aliquot of supernatant liquid had been removed for light output measurement in accordance with the method of Tung et al. The $\Gamma$ for the 10% sample was determined to be 22, which means that only 4.3% of the light remained in that supernatant compared to that in the control test tube. The results of the plate count tests indicated that about 95%±5% of the bacteria present in the control supernatant were in/on the settled solids, and only about 5% were left in the supernatant liquid from the 10% (W/V) test tube. This result confirmed, therefore, that the response to the clean soil obtained from the U.S. EPA was primarily due to interference from factors 1 and 2, rather than to actual toxicity.

Experiments with multiple control test tubes indicated a mean loss of 10% of the bacteria due to filtration. This loss is, in principal, canceled in data handling by use of a filtered control. However, if the filter loss is dependent on the concentration of solids in each sample, there should also be an effect of filtration on the slope of the log-log dose-response curve. The results shown in Tables 2 and 3 confirm that the raw data slopes differ by about 1.7 times the sum of their standard deviations, making it probable that they are indeed different. In addition, the IC50s of Table 4 indicate that the apparent toxicities for the filtered and unfiltered reference files are different, with 95% confidence, since neither mean falls within the 95% confidence interval of the other. Also, when reference file SPTREF01 is reduced using the unfiltered file CSREFNF2 as reference the result is a 95% confidence range of 8 to 15% (W/V) for the apparent IC50 of filtered clean soil against unfiltered. The relative responses are essentially zero up to 1.23% (W/V), then create a monotonically increasing response up to 9.87% (W/V), which is the highest concentration tested, having a best log-log line slope of 1.082. This result is consistent with a filter loss which increases with particle concentration.

Finally, it should be noted that the most reliable data for SARM II are those with the LSP of Table 3, which happen to have been unfiltered. The most meaningful relative response data are, therefore, against reference file CSREFNF2, which is also unfiltered. The second most reliable relative data for SARM II should be that with filtering and the SSP from Table 2, against reference file SPTREF01, which also used filtration. By the teaching of the present procedure, it would be expected that this result would agree with that without filtration for either data set, but they differ by a factor of (1.79/1.088)=1.65. However, the standard deviation for the SSP SARM II data is so large that no significance can be attached to this apparent anomaly, and the disagreement serves to prove the point that the LSP is important if one desires to obtain Solid-Phase Test precision comparable to that normally achieved with the Microtox system for liquid samples. Additional tests using a combination of filtered and unfiltered LSP SARM II data against the filtered and unfiltered LSP reference files would be required to prove that filtration does not degrade the results significantly, but it can be fairly concluded that it might be feasible to eliminate filtration except for samples containing low density particles which do not settle.

TABLE 1

Raw Test Results For SARM I (Without Reference) And Also The Results Using Three Mean Clean Soil Reference Files, One From Replicate Small Samples And Two From Replicate Aliquots From Large Sample Suspensions, One With And One Without Filtration.

| TEST FILE | IC50 AND 95% CONFIDENCE RANGE, % (W/V) | | | SLOPE OF LOG-LOG PLOT |
|---|---|---|---|---|
| | IC50 | LOW | HIGH | |
| RAW SARM I DATA (SMALL SAMPLES, FILTER USED) | | | | |
| 1112003 | 0.0408 | 0.0399 | 0.0417 | 1.4346 |
| 1112004 | 0.0352 | 0.0305 | 0.0407 | 1.2571 |
| 1112005 | 0.0397 | 0.0392 | 0.0401 | 1.3791 |
| 1112006 | 0.0358 | 0.0337 | 0.0380 | 1.3351 |
| MEAN VALUE | 0.038 | 0.036 | 0.040 | 1.351 |
| STD. DEV. | 0.002 | 0.004 | 0.001 | 0.065 |
| % COEF. VAR. | 6.4 | 10.9 | 3.4 | 4.8 |
| SARM I DATA (SMALL SAMPLES, FILTERED) AGAINST FILE NORMALCS | | | | |
| 91112003 | 0.0411 | 0.0342 | 0.0496 | 1.3289 |
| 91112004 | 0.0397 | 0.0357 | 0.0440 | 1.2429 |
| 91112005 | 0.0416 | 0.0390 | 0.0443 | 1.3033 |
| 91112006 | 0.0341 | 0.0314 | 0.0369 | 1.1733 |
| MEAN VALUE | 0.039 | 0.035 | 0.044 | 1.262 |
| STD. DEV. | 0.003 | 0.003 | 0.005 | 0.060 |
| % COEF. VAR. | 7.6 | 7.8 | 3.3 | 4.8 |
| SARM I DATA (SMALL SAMPLES, FILTERED) AGAINST FILE SPTREF01 | | | | |
| 91112003 | 0.0375 | 0.0307 | 0.0457 | 1.2871 |
| 91112004 | 0.0368 | 0.0329 | 0.0413 | 1.2417 |
| 91112005 | 0.0391 | 0.0365 | 0.0420 | 1.3115 |
| 91112006 | 0.0344 | 0.0324 | 0.0364 | 1.2429 |
| MEAN VALUE | 0.037 | 0.033 | 0.041 | 1.271 |
| STD. DEV. | 0.002 | 0.002 | 0.003 | 0.030 |
| % COEF. VAR. | 4.6 | 6.4 | 8.0 | 2.3 |
| SARM I DATA (SMALL SAMPLES, FILTERED) AGAINST FILE CSREFNF2 | | | | |
| 91112003 | 0.0368 | 0.0297 | 0.0456 | 1.2943 |
| 91112004 | 0.0362 | 0.0321 | 0.0407 | 1.2488 |
| 91112005 | 0.0384 | 0.0352 | 0.0419 | 1.3177 |
| 91112006 | 0.0344 | 0.0327 | 0.0362 | 1.2676 |
| MEAN VALUE | 0.036 | 0.032 | 0.041 | 1.282 |
| STD. DEV. | 0.001 | 0.002 | 0.003 | 0.026 |
| % COEF. VAR. | 3.9 | 6.0 | 8.2 | 2.0 |

TABLE 2

Raw Test Results For SARM II (Without Reference) In Tests Using Replicate Small Samples And Filter Separation, And Also The Results With Two Mean Clean Soil Reference Files Obtained Using Groups Of Ten Replicates Each From Several Larger Samples, One Group With And One Without Filter Separation Of The Bacteria After Exposure To The Solid-Phase Sample.

| TEST FILE | IC50 AND 95% CONFIDENCE RANGE, % (W/V) | | | SLOPE OF LOG-LOG PLOT |
|---|---|---|---|---|
| | IC50 | LOW | HIGH | |
| RAW SARM II DATA (SMALL SAMPLES, FILTER USED) | | | | |
| 09239102 | 0.6336 | 0.4778 | 0.8403 | 0.9249 |
| 09239103 | 0.7810 | 0.7188 | 0.8485 | 1.1475 |
| 09239104 | 0.5417 | 0.4696 | 0.6248 | 0.9796 |
| 09249101 | 0.5833 | 0.4927 | 0.6906 | 1.0483 |

TABLE 2-continued

Raw Test Results For SARM II (Without Reference) In Tests Using Replicate Small Samples And Filter Separation, And Also The Results With Two Mean Clean Soil Reference Files Obtained Using Groups Of Ten Replicates Each From Several Larger Samples, One Group With And One Without Filter Separation Of The Bacteria After Exposure To The Solid-Phase Sample.

| TEST FILE | IC50 AND 95% CONFIDENCE RANGE, % (W/V) | | | SLOPE OF LOG-LOG PLOT |
|---|---|---|---|---|
| | IC50 | LOW | HIGH | |
| 09249102 | 0.7297 | 0.6163 | 0.8638 | 1.1690 |
| MEAN VALUE | 0.654 | 0.555 | 0.774 | 1.074 |
| STD. DEV. | 0.089 | 0.098 | 0.097 | 0.101 |
| % COEF. VAR. | 13.7 | 17.6 | 12.6 | 9.4 |
| SARM II DATA (SMALL SAMPLES, FILTERED) AGAINST FILE NORMALCS | | | | |

(Note: This reference file did not provide useful results for SARM II, probably because use of an excess of fine components for these clean soil tests caused the reference to appear too toxic, resulting in an over correction. See Table 4 for example data.)

| | IC50 | LOW | HIGH | |
|---|---|---|---|---|
| SARM II DATA (SMALL SAMPLE, FILTERED) AGAINST FILE SPTREF01 | | | | |
| 09239102 | 1.4109 | 0.9127 | 2.1810 | 0.7739 |
| 09239103 | 2.6226 | 1.2795 | 5.3757 | 0.7203 |
| 09239104 | 1.1699 | 0.9136 | 1.498 | 0.6613 |
| 09249101 | 1.2651 | 1.2483 | 1.2823 | 1.1068 |
| 09249102 | 2.4821 | 1.2976 | 4.7476 | 0.6778 |
| MEAN VALUE | 1.790 | 1.130 | 3.017 | 0.7880 |
| STD. DEV. | 0.629 | 0.178 | 1.707 | 0.164 |
| % COEF. VAR. | 35.1 | 15.8 | 56.6 | 20.8 |
| SARM II DATA (SMALL SAMPLE, FILTERED) AGAINST FILE CSREFNF2 | | | | |
| 09239102 | 1.2279 | 1.0448 | 1.4430 | 0.6766 |
| 09239103 | 2.0272 | 1.3931 | 2.9499 | 0.6449 |
| 09239104 | 0.8136 | 0.7129 | 0.9284 | 0.8153 |
| 09249101 | 0.7576 | 0.6219 | 0.9230 | 0.9861 |
| 09249102 | 1.8781 | 1.5558 | 2.2673 | 0.6321 |
| MEAN VALUE | 1.341 | 1.066 | 1.7020 | 0.751 |
| STD. DEV. | 0.527 | 0.366 | 0.7940 | 0.134 |
| % COEF. VAR. | 39.3 | 34.3 | 46.6 | 17.9 |

TABLE 3

Raw Test Results For SARM II (Without Reference) In Tests Using Replicates Taken From One Large Suspended Sample And Without Filter Separation, And Also The Results When Using Two Mean Clean Soil Reference Files Obtained Using Groups Of Ten Replicates Each From Several Large Sample Suspensions, One Group With And One Without Filter Separation Of The Bacteria After Exposure To The Solid-Phase Sample.

| TEST FILE | IC50 AND 95% CONFIDENCE RANGE, % (W/V) | | | SLOPE OF LOG-LOG PLOT |
|---|---|---|---|---|
| | IC50 | LOW | HIGH | |
| RAW SARM II DATA (ONE LARGE SAMPLE SUSPENSION, NO FILTERS) | | | | |
| 92011605 | 0.7225 | 0.6860 | 0.7610 | 1.4560 |
| 92011606 | 0.6811 | 0.5992 | 0.7743 | 1.6021 |
| 92011701 | 0.6178 | 0.5450 | 0.7004 | 1.2851 |
| 92011702 | 0.6746 | 0.6445 | 0.7061 | 1.4053 |
| MEAN VALUE | 0.674 | 0.619 | 0.735 | 1.437 |
| STD. DEV. | 0.037 | 0.052 | 0.033 | 0.114 |
| % COEF. VAR. | 5.5 | 8.5 | 4.4 | 7.9 |
| SARM II DATA (LARGE SAMPLE, UNFILTERED) AGAINST FILE NORMALCS | | | | |

(Note: This reference file did not provide useful results for SARM II, probably because use of an excess of fine components for these clean soil tests caused the reference to appear too toxic, resulting in an over correction. See Table 4 for example data.)

| SARM II DATA (LARGE SAMPLE, UNFILTERED) AGAINST FILE SPTREF01 | | | | |
|---|---|---|---|---|
| 92011605 | 1.4252 | 1.3820 | 1.4698 | 0.8954 |
| 92011606 | 1.3929 | 1.2005 | 1.6160 | 1.0500 |
| 92011701 | 1.1452 | 0.8958 | 1.4641 | 0.9344 |
| 92011702 | 1.2803 | 1.0750 | 1.5246 | 1.0681 |
| MEAN VALUE | 1.311 | 1.138 | 1.519 | 0.987 |
| STD. DEV. | 0.110 | 0.178 | 0.061 | 0.074 |
| % COEF. VAR. | 8.4 | 15.6 | 4.0 | 7.5 |
| SARM II DATA (LARGE SAMPLE, UNFILTERED) AGAINST FILE CSREFNF2 | | | | |
| 92011605 | 1.1493 | 1.0741 | 1.2298 | 1.0385 |
| 92011606 | 1.1513 | 1.0731 | 1.2352 | 1.0063 |
| 92011701 | 0.9949 | 0.7586 | 1.1769 | 1.0414 |
| 92011702 | 1.0576 | 0.9291 | 1.2038 | 1.1636 |
| MEAN VALUE | 1.088 | 0.959 | 1.211 | 1.062 |
| STD. DEV. | 0.066 | 0.130 | 0.023 | 0.060 |
| % COEF. VAR. | 6.1 | 13.5 | 1.9 | 5.6 |

TABLE 4

Concentrations of Sample and Γ Responses For Some Of The Test Results Presented In Table 2, Showing Over Compensation Of A Typical SARM II Test By Reference Data File NORMALCS, For Which Larger Particles Were Avoided During Sample Aliquot Selection.

| | MEAN OBSERVED CLEAN SOIL Γ | | | ONE SARM II FILE | | |
|---|---|---|---|---|---|---|
| CONC. % (W/V) | FILTERED 14-SMALL NORMALCS | FILTERED 10-LARGE SPTREF01 | UNFILT. 10-LARGE CSREFNF | FILTERED 09239102 RA | FILTERED 09239102/ NORMALCS | FILTERED 09239102/ SPTREF01 |
| 0.0048 | 0.0298 | 0.0490 | 0.0391 | 0.1632 | 0.1309 | 0.1102 |
| 0.0096 | 0.0130 | 0.0377 | 0.0508 | 0.0358 | 0.0238 | −0.0006 |
| 0.0193 | 0.0114 | 0.0246 | 0.0149 | 0.0284 | 0.0180 | 0.0049 |
| 0.0385 | 0.0371 | 0.0227 | 0.0223 | 0.0724 | 0.0353 | 0.0499 |
| 0.0771 | 0.0700 | 0.0243 | 0.0016 | 0.1293 | 0.0566 | 0.1038 |
| 0.1524 | 0.1325 | 0.0715 | 0.0227 | 0.2903 | 0.1407 | 0.2057 |
| 0.3084 | 0.2641 | 0.1072 | 0.0798 | 0.4688 | 0.1633 | 0.3281 |
| 0.6168 | 0.6920 | 0.2229 | 0.1734 | 0.9024 | 0.1257 | 0.5575 |

TABLE 4-continued

Concentrations of Sample and Γ Responses For Some Of
The Test Results Presented In Table 2, Showing Over
Compensation Of A Typical SARM II Test By Reference
Data File NORMALCS, For Which Larger Particles Were
Avoided During Sample Aliquot Selection.

| | MEAN OBSERVED CLEAN SOIL Γ | | | ONE SARM II FILE | | |
|---|---|---|---|---|---|---|
| CONC. % (W/V) | FILTERED 14-SMALL NORMALCS | FILTERED 10-LARGE SPTREF01 | UNFILT. 10-LARGE CSREFNF | FILTERED 09239102 RA | FILTERED 09239102/ NORMALCS | FILTERED 09239102/ SPTREF01 |
| 1.2335 | 2.6887 | 0.6929 | 0.5535 | 1.9851 | −0.1898 | 0.7653 |
| 2.4670 | 12.2626 | 2.7764 | 2.1066 | 6.0359 | −0.4689 | 0.8653 |
| 4.9340 | 33.2466 | 10.2613 | 7.1301 | 31.3024 | −0.0557 | 1.8718 |
| 9.8680 | 84.4701 | 35.9004 | 18.4175 | 347.1481 | 3.0781 | 8.4459 |
| IC50 = | 0.6890 | 1.4299 | 1.6581 | 0.6336 | (?) | 1.4109 |
| LOW = | 0.5883 | 1.3493 | 1.5603 | 0.4778 | | .9127 |
| HIGH = | 0.8071 | 1.5154 | 1.7620 | 0.8403 | | 2.1810 |
| SLOPE = | 1.8100 | 1.8551 | 1.8013 | 0.9249 | (?) | 0.7739 |

As will be understood by those skilled in the art, various arrangements other than those described in detail in the specification will occur to those persons skilled in the art which arrangements lie within the spirit and scope of the invention. It is therefore to be understood that the invention is to be limited only by the claims appended hereto.

What is claimed is:

1. A method of obtaining small representative solid-phase samples from a large solid-phase particulate sample, which method comprises the steps of:

mixing an initial solid-phase particulate sample to assure homogeneity;

selecting a portion of said mixed solid-phase particulate sample to provide a representative intermediate size sample;

suspending said intermediate particulate sample in a volume of liquid diluent in a first vessel;

agitating said suspension to promote separation of such solid particles as may be adhering to other particles to obtain a homogeneous suspension;

transferring a fraction of said homogeneous suspension to a second vessel in order to provide a representative small particulate sample; wherein said agitating is carried out using a magnetic stirring bar in the first vessel to create a magnetic stirring zone; and wherein said stirring is carried out at a speed such as to create a vortex cone height equal to 30% to 70% of the greater depth of the suspension at the outer edge region of said stirring zone and said small representative solid-phase particulate sample is removed while stirring under such conditions.

2. The method of claim 1 wherein a plurality of fractions of said homogeneous suspension are transferred to other vessels to provide a plurality of said representative small samples for replicate tests.

3. The method of claim 1 wherein said first vessel has a volume in the range of about 20 to 100 ml, said intermediate sample weighs between about 3 and 15 grams, and said volume of liquid diluent is between about 15 and 75 ml.

4. The method of claim 1 wherein a plurality of said fractions are transferred to a plurality of said second vessels to provide a plurality of small representative samples which are thereafter analyzed as replicate tests.

5. The method of claim 1 wherein said small representative sample is removed with a pipette having a tip aperture of at least 1.5 mm and not greater than about 2.5 mm, with the tip positioned a distance above the bottom of said first vessel at least about three times the height of the top of the rotating stir bar, and at a location generally close to the vertical wall of said first vessel.

6. The method of claim 5 wherein said first vessel has a volume in the range of about 20 to 100 ml, said intermediate sample weighs between about 3 and 15 grams, and said volume of diluent is between about 15 and 75 ml.

7. The method of claim 6 wherein a plurality of said fractions are transferred to a plurality of said second vessels to provide a plurality of small representative samples which are thereafter analyzed for toxicity using luminescent bacteria as replicate tests.

8. A method of obtaining small representative solid-phase samples from a large solid-phase particulate sample, which method comprises the steps of:

a. separating solid-phase material from any liquid-phase as may be present to obtain an initial large solid-phase particulate sample;

b. mixing said initial solid-phase particulate sample to assure homogeneity;

c. selecting a portion of said mixed solid-phase particulate sample which provides an intermediate size representative sample;

d. forming a suspension of said intermediate particulate sample in a volume of liquid diluent contained in a first vessel;

e. agitating said suspension to promote separation of such solid particles as may be adhering to other particles to obtain a homogeneous suspension;

f. transferring a fraction of said homogeneous suspension to a second vessel which will constitute a small representative solid-phase particulate sample; wherein said agitating is carried out using a magnetic stirring bar in the first vessel to create a magnetic stirring zone; and wherein said stirring is carried out at a speed such as to create a vortex cone height equal to 30% to 70% of the greater depth of the suspension at the outer edge region of said stirring zone and said small representative solid-phase particulate sample is removed while stirring under such conditions.

9. The method of claim 8 wherein additional fractions of said homogeneous suspension are transferred to provide a plurality of said small representative samples for replicate tests.

10. The method of claim 8 wherein said first vessel has a volume in the range of about 20 to 100 ml, said intermediate sample weighs between about 3 and 15 grams, and said volume of liquid diluent is between about 15 and 75 ml.

11. The method of claim 8 wherein a plurality of said fractions are transferred to a plurality of said second vessels to provide a plurality of small representative samples which are thereafter analyzed as replicate tests.

12. The method of claim 8 wherein said small representative sample is removed with a pipette having a tip aperture of at least 1.5 mm and not greater than about 2.5 mm, with the tip positioned a distance above the bottom of said first vessel at least about three times the height of the top of the rotating stir bar, and at a location generally close to the vertical wall of said first vessel.

13. The method of claim 12 wherein said first vessel has a volume in the range of about 20 to 100 ml, said intermediate sample weighs between about 3 and 15 grams, and said volume of diluent is between about 15 and 75 ml.

14. The method of claim 13 wherein a plurality of said fractions are transferred to a plurality of said second vessels to provide a plurality of small representative samples which are thereafter analyzed for toxicity using luminescent bacteria as replicate tests.

* * * * *